US011103631B2

(12) United States Patent
Ou Yang et al.

(10) Patent No.: US 11,103,631 B2
(45) Date of Patent: Aug. 31, 2021

(54) NASAL ASPIRATOR WITH LIGHTING FUNCTION

(71) Applicant: AVITA CORPORATION, New Taipei (TW)

(72) Inventors: Hsing Ou Yang, New Taipei (TW); Hsuan Hao Shih, New Taipei (TW); Ta Chieh Yang, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 387 days.

(21) Appl. No.: 15/394,830

(22) Filed: Dec. 30, 2016

(65) Prior Publication Data

US 2017/0189590 A1 Jul. 6, 2017

(30) Foreign Application Priority Data

Dec. 30, 2015 (TW) .................................. 104221090

(51) Int. Cl.
*A61M 1/00* (2006.01)
(52) U.S. Cl.
CPC ............ *A61M 1/80* (2021.05); *A61M 1/0003* (2013.01); *A61M 2205/587* (2013.01); *A61M 2205/8206* (2013.01); *A61M 2210/0618* (2013.01)
(58) Field of Classification Search
CPC .............. A61M 1/0066; A61M 1/0003; A61M 2205/587; A61M 2210/0618
See application file for complete search history.

(56) References Cited

U.S. PATENT DOCUMENTS

| 2003/0109854 | A1* | 6/2003 | Chen | A61M 1/0023 |
| | | | | 604/540 |
| 2008/0125838 | A1* | 5/2008 | Francis | A61M 27/006 |
| | | | | 607/92 |
| 2011/0282268 | A1* | 11/2011 | Baker | A61B 17/24 |
| | | | | 604/20 |

FOREIGN PATENT DOCUMENTS

| CN | 2502701 | | 7/2002 |
| KR | 20000032005 A | * | 6/2000 |

* cited by examiner

*Primary Examiner* — Tatyana Zalukaeva
*Assistant Examiner* — Jessica R Arble
(74) *Attorney, Agent, or Firm* — Raymond Y. Chan; David and Raymond Patent Firm (57) ABSTRACT

The present disclosure illustrates a nasal aspirator with a lighting function. The nasal aspirator includes a main body, a power supply unit, a sucking unit, air extracting unit, and a lighting unit. The power supply unit is disposed in the main body. The sucking unit is coupled with and extended out of the main body and configured to insert into a nasal cavity. The air extracting unit is disposed in the main body and electrically coupled with the power supply unit, and configured to enable the sucking unit to generate suction. The lighting unit is disposed in the sucking unit, and the power supply unit is configured to drive the air extracting unit and the lighting unit.

9 Claims, 8 Drawing Sheets

FIG. 8

NASAL ASPIRATOR WITH LIGHTING FUNCTION

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present disclosure relates to a nasal aspirator with a lighting function. More particularly, the present disclosure relates to a nasal aspirator which is usable in dark or night environment.

Description of Related Arts

For infants, young children or patients who are unable to take care of themselves and blow nose, snot may be stuck in their nasal cavities and cause problem in breathing difficulties. For this reason, a device capable of sucking snot is developed to solve the problem. For example, Taiwan patent No. 229438, titled "nasal aspirator", discloses a manual nasal aspirator. The manual nasal aspirator includes a suction head, an elastic capsule, a first valve interlinked between a bottom part of the suction head and the elastic capsule, and a second valve formed at a bottom part of the elastic capsule. In order to operate the nasal aspirator, the user can compress the elastic capsule to separately operate the first valve and the second valve, thereby sucking snot. The conventional nasal aspirator can be continuously compressed to suck snot by manual operation only, so it is not convenient enough in use. Furthermore, Taiwan patent No. 437394, titled "electronic nasal aspirator", discloses an electronic nasal aspirator in which a turning wheel with an eccentric shaft is mounted on a rotor of a small DC motor. While the eccentric shaft is rotating, the turning wheel can continuously expand and compress a soft rubber pad to perform function of inhaling and exhausting air; in addition, upper and lower valves of a rubber sheet are used to control an inlet aperture and an outlet aperture to inhale or exhaust unidirectionally. Furthermore, an inlet tube is interlinked with a collecting container for collecting snot.

The nasal aspirator has been developed from manual nasal aspirator to electronic nasal aspirator, in order to continuously and quickly clean the snot in nasal cavity; However, in indoor lighting environment, it is dark inside the nasal cavity and not easy to observe nasal cavity clearly, and the infant or young child usually fears the nasal aspirator, so parents usually clean nasal cavity of infant or young child who falls asleep. In order to prevent from waking the infant or the young child who falls asleep, parents use the nasal aspirator to clean the nasal cavity of infant or young child in night or dark environment more usually. For this reason, a flashlight is required for lighting, but it is inconvenient for single user to hold the infant or the young child, operate the nasal aspirator and hold the flashlight at the same time. Furthermore, even if the infant or the young child sleeps in indoor environment at night, frequently turning on room light may disturb sleep of the infant or the young child. A general indoor lamp is hard to light the nasal cavity, so the adult patient who needs nursing care is not easy to suck snot completely subject to lack of light, and it may cause damage of nasal mucosa of the adult patient.

SUMMARY OF THE PRESENT INVENTION

Therefore, it is a primary objective of the present disclosure to provide a nasal aspirator with lighting function, in order to solve the problems that it is inconvenient to use the conventional nasal aspirator for patient, infant, young child or old person under the night or dark environment without lighting; and frequently turning on lamp may disturb sleep of the infant or young child.

According to embodiment of the present disclosure, a nasal aspirator with a lighting function includes a main body, a power supply unit, a sucking unit, and air extracting unit, and a lighting unit. The power supply unit is disposed in the main body. The sucking unit is coupled with and extended out of the main body and configured to insert into a nasal cavity. The air extracting unit is disposed in the main body and electrically coupled with the power supply unit, and configured to enable the sucking unit to generate suction. The lighting unit is disposed in the sucking unit, and the power supply unit is configured to drive the air extracting unit and the lighting unit.

Preferably, the nasal aspirator of present disclosure provides the power supply unit being in contact with the air extracting unit and the lighting unit through electrodes, to provide power.

Preferably, the nasal aspirator of present disclosure further includes a sensing module which includes a first electromagnetic induction device and a second electromagnetic induction device separately disposed in the main body and the sucking unit. The first electromagnetic induction device is electrically coupled with the power supply unit, and when the power supply unit provides power to drive the first electromagnetic induction device, the second electromagnetic induction device are triggered to enable the lighting unit to emit light.

Therefore, the present disclosure provides the nasal aspirator with the lighting function, the nasal aspirator includes the light-emitting element to illuminate the inside of the nasal cavity, so that the nasal aspirator can be used in the dark or night environment more easily to avoid damage of nasal mucosa or bleeding caused by the nasal aspirator.

BRIEF DESCRIPTION OF THE DRAWINGS

The structure, operating principle and effects of the present disclosure will be described in detail by way of various embodiments which are illustrated in the accompanying drawings.

DETAILED DESCRIPTION OF THE PREFERRED EMBODIMENT

The following embodiments of the present invention are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present invention. As used herein, the term "or" includes any and all combinations of one or more of the associated listed items.

Figure 1:
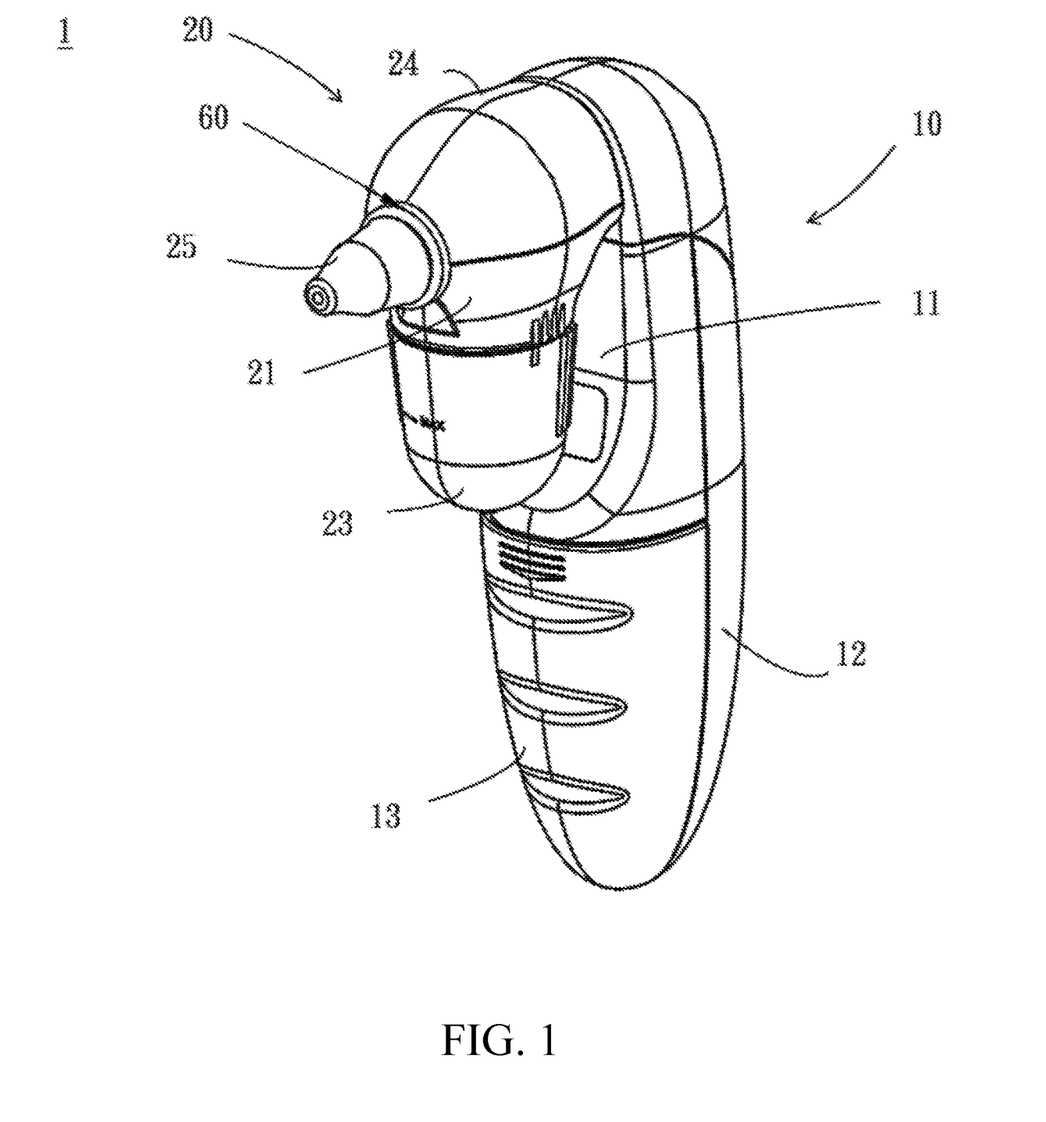
FIG. 1 is a perspective view of a first embodiment of a nasal aspirator with lighting function of the present disclosure.
Figure 2:
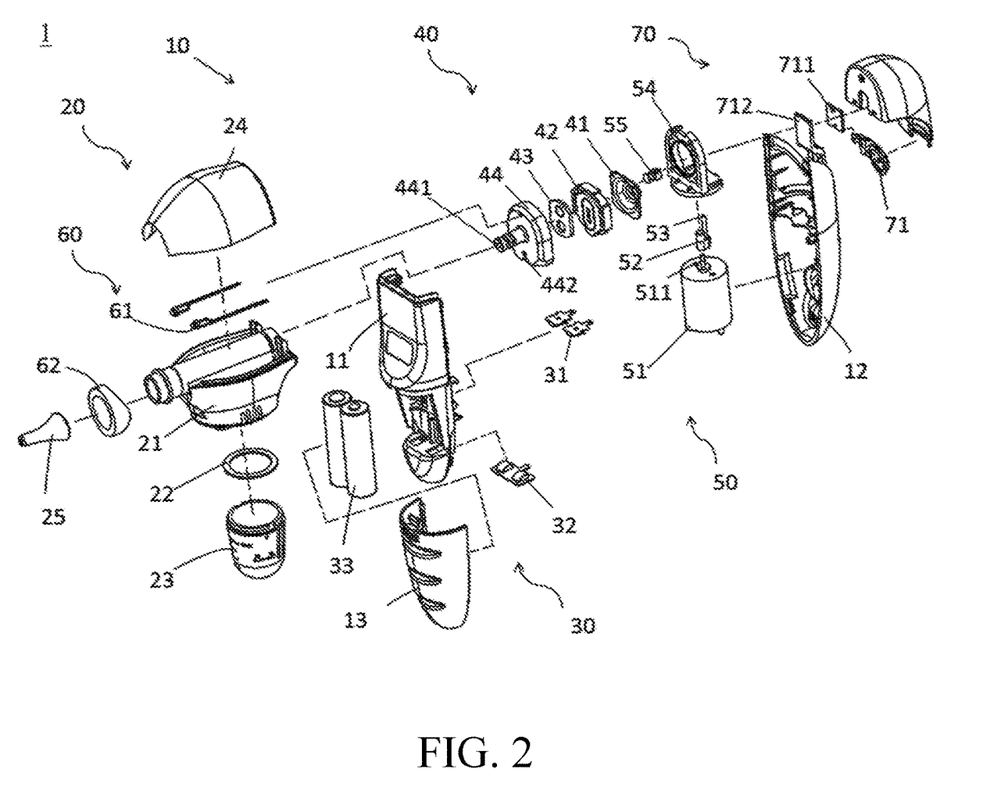
FIG. 2 is an exploded view of the first embodiment of the nasal aspirator of the present disclosure.

Please refer to FIGS. 1 and 2, which show a first preferred embodiment of a nasal aspirator with a lighting function of the present disclosure. A nasal aspirator 1 includes a main body 10, a sucking unit 20, a power supply unit 30, an air extracting unit 50 and a lighting unit 60. The main body 10 includes a first shell member 11, a second shell member 12 and a cover 13. In this embodiment, the first shell member 11 is a front shell member of the nasal aspirator 1, the second shell member 12 is a rear shell member of the nasal aspirator 1, and the cover 13 is a battery lid.

Please refer to FIG. 2. The sucking unit 20 is coupled with and extended out of the main body 10, and configured to insert a nasal cavity of human body to suck snot. The sucking unit 20 further includes a sucking part 21, a sealing washer 22, a collecting container 23, a top lid 24 and a suction head 25. The sealing washer 22 is combined with the collecting container 23 under the sucking part 21, and the suction head 25 can be inserted into the nasal cavity of human body to suck snot, and the sucked snot is collected in the collecting container 23. The lighting unit 60 is disposed in the sucking unit 20. In this embodiment, the lighting unit 60 and the suction head 25 are combined and disposed in the front of the sucking part 21, and covered by the top lid 24, thereby forming the sucking unit 20 integrally.

The lighting unit 60 includes a light-emitting element 61 which can be a solid state light source or a gaseous light source, such as a light-emitting diode or a bulb, upon design demand. The sucking unit 20 includes an optical conductor 62 for conducting light generated from the lighting unit 60. Preferably, the optical conductor 62 can be in an annular shape, a pillar shape, or a tapered shape. In this embodiment, an annular-shaped optical conductor is taken as an example for illustration. The light emitted by the light-emitting element 61 is conducted to the outside through the optical conductor 62. Alternatively, in order to conduct light generated from the lighting unit 60, the suction head 25 can be an optical conductor or includes light guide material without extra using the optical conductor.

The power supply unit 30 is disposed in a space formed between the first shell member 11 of the main body 10 and the cover 13, and configured to drive the air extracting unit 50 and the lighting unit 60. In this embodiment, the power supply unit 30 is electrically coupled with the air extracting unit 50 and the lighting unit 60 through electrodes for providing power. The power supply unit 30 includes a first electrode set 31, a second electrode set 32 and a battery set 33. The first electrode set 31 and the second electrode set 32 are mounted on the first shell member 11, and the battery set 33 provides power through the first electrode set 31 and the second electrode set 32.

The air extracting unit 50 is disposed in the main body 10, and includes an air pump 40 configured to enable the sucking unit 20 to have a negative pressure function. The air pump 40 includes a chuck 41, a holder 42, a non-return valve 43, and an air extracting part 44 which includes an air inlet 441 and an air outlet 442. The air pump 40 further includes a DC motor 51, an eccentric part 52, an eccentric shaft 53, an air pump connecting member 54 and a chuck connecting member 55. The DC motor 51 is electrically coupled with the power supply unit 30, and includes a rotating shaft 511, and all of the rotating shaft 511, the eccentric part 52 and the eccentric shaft 53 form an eccentric mechanism which is inserted through the air pump connecting member 54 to interlink with the chuck connecting member 55, and the chuck connecting member 55 is interlinked with the chuck 41.

The nasal aspirator 1 of the present disclosure further includes a control unit 70, a power switch 71 and a switch (not shown in figures). The power switch 71 includes a plate 711 and a plate frame 712. The control unit 70 is disposed in the main body 10 and electrically coupled with the air extracting unit 50 and the lighting unit 60. Through the control unit 70, the power switch 71 and the switch can be used to drive the air extracting unit 50 and the lighting unit 60.

The process of operating the nasal aspirator 1 of the present disclosure will be described in the following.

In order to use the nasal aspirator 1 with the lighting function, the user can press the power switch 71, and the power switch 71 then drives the lighting unit 60 and the air extracting unit 50 (for example, the air pump 40 of the air extracting unit 50) at the same time through the control unit 70, so that the lighting unit 60 can emit light to facilitate alignment of the suction head 25 with the nasal cavity for sucking snot. Alternatively, by using the switch, the control unit 70 can control the lighting unit 60 to drive the light-emitting element 61, and after the suction head 25 is aligned with and inserted into the nasal cavity, the air pump 40 is driven to suck snot. It is appreciated that, upon design demand, the switch can be used to drive the air extracting unit 50 and the lighting unit 60 at the same time or one after another. It is to be noted that the power supply unit 30 is in contact with the air extracting unit 50 and the lighting unit 60 through the electrodes for providing power during the process of operating the nasal aspirator 1.

Figure 3:
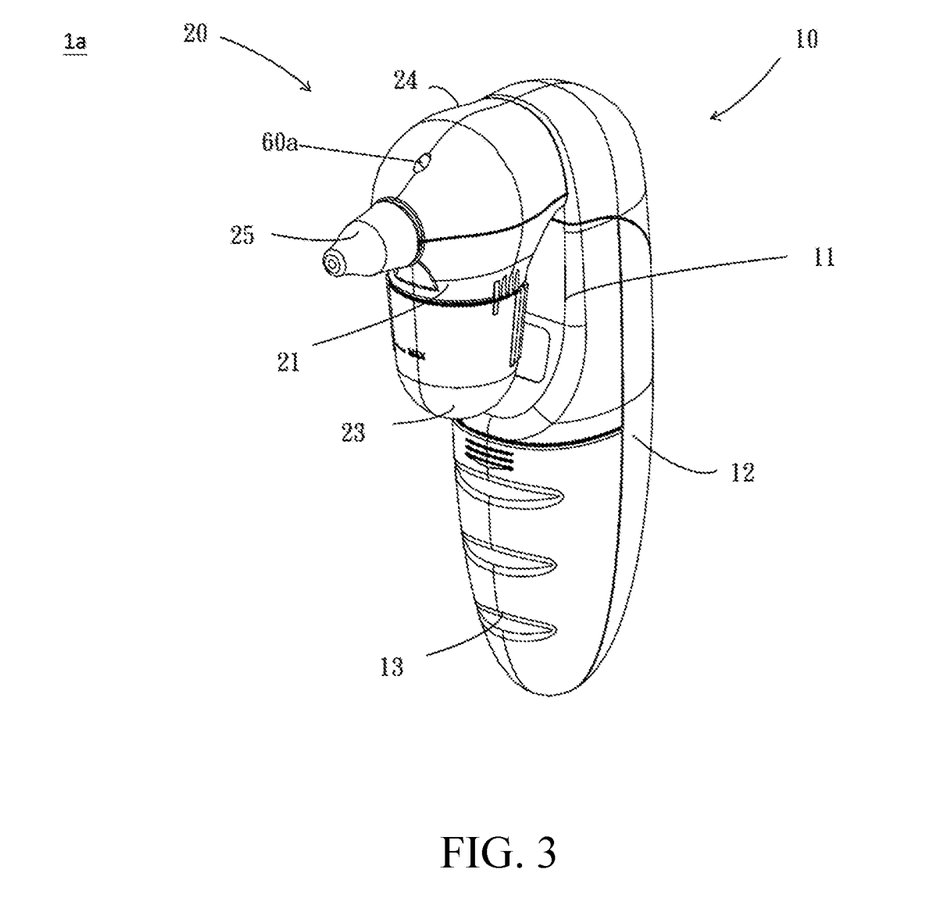
FIG. 3 is a perspective view of modification of the first embodiment of the nasal aspirator of the present disclosure.
Figure 4:
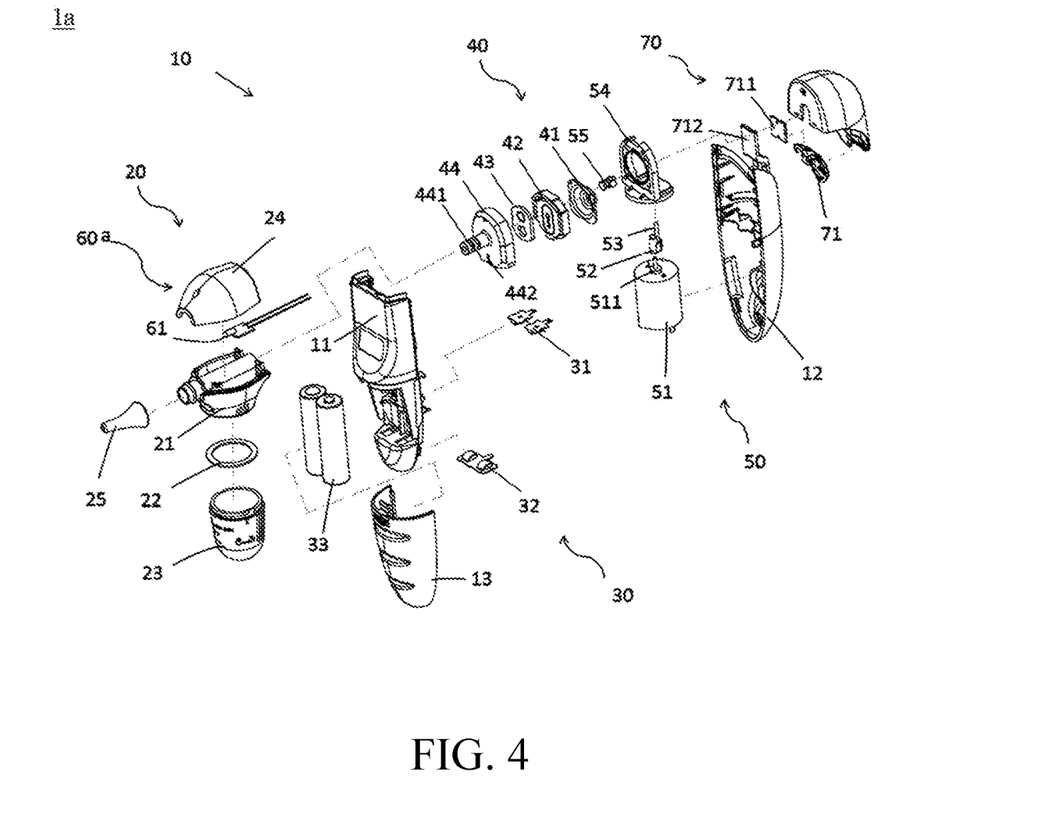
FIG. 4 is an exploded view of modification of the first embodiment of the nasal aspirator of the present disclosure.

Please refer to FIGS. 3 and 4, which show modification of the first preferred embodiment of the nasal aspirator 1 of the present disclosure. Major elements of the nasal aspirator 1a are the same as that of the nasal aspirator 1, so their detailed descriptions are not repeated. The difference between the nasal aspirator 1a and the nasal aspirator 1 is that the light-emitting element 61 of the lighting unit 60a of the nasal aspirator 1a is directly mounted on the top lid 24 of the sucking unit 20, in order to directly illuminate the nasal cavity through an opening of the top lid. The nasal aspirator 1a has advantage in simpler structure of the lighting unit 60a for easier production.

Figure 5:
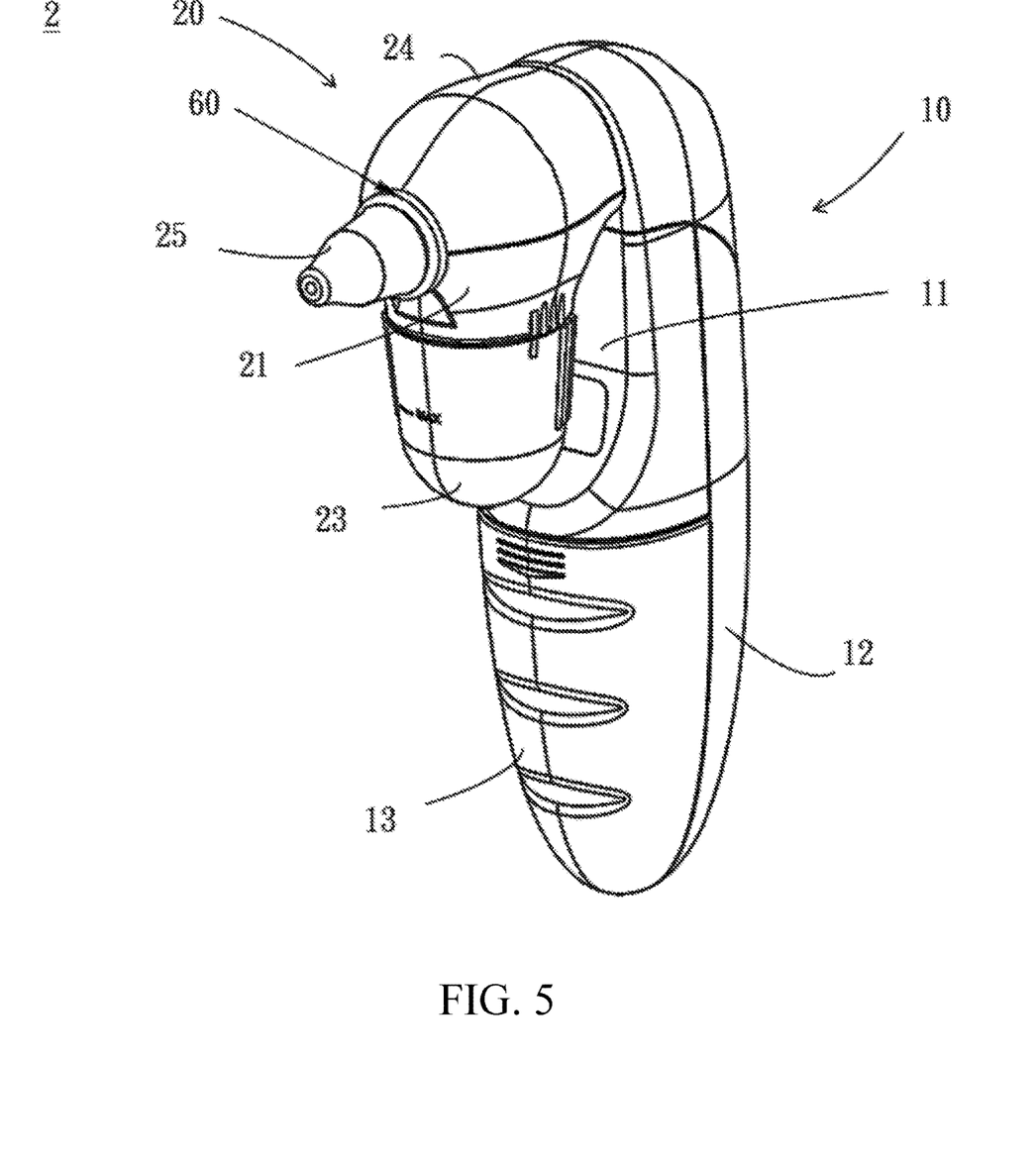
FIG. 5 is a perspective view of a second embodiment of a nasal aspirator with lighting function of the present disclosure.
Figure 6:
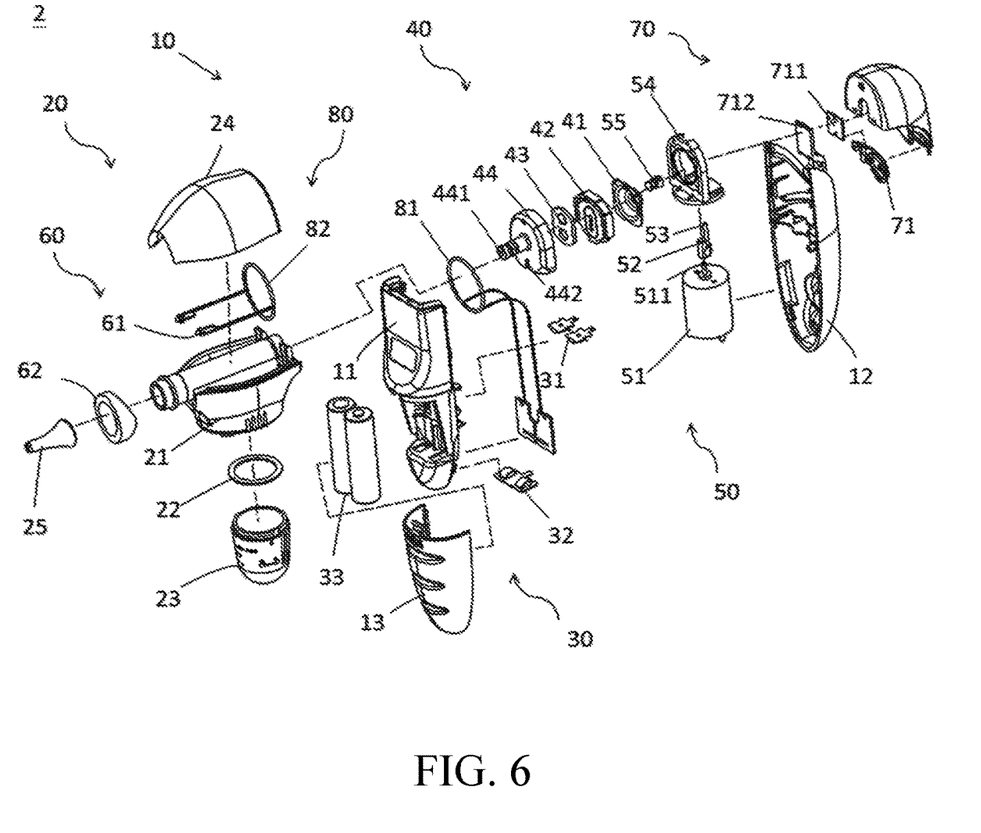
FIG. 6 is an exploded view of the second embodiment of the nasal aspirator of the present disclosure.

Please refer to FIGS. 5 and 6, which show a second embodiment of the nasal aspirator of the present disclosure. A nasal aspirator 2 includes a main body 10, a sucking unit 20, a power supply unit 30, an air extracting unit 50 and a lighting unit 60. The main body 10 includes a first shell member 11, a second shell member 12 and a cover 13. In this embodiment, the first shell member 11 is a front shell member of the nasal aspirator 2, the second shell member 12 is a rear shell member of the nasal aspirator 2, and the cover 13 is a battery lid of the nasal aspirator 2. Major elements of the nasal aspirator 2 are the same as that of the nasal aspirator 1, so their detailed descriptions are not repeated. The difference between the nasal aspirator 2 and the nasal aspirator 1 is that the nasal aspirator 2 further includes a sensing module 80 including a first electromagnetic induction device 81 and a second electromagnetic induction device 82, as shown in FIG. 6. The first electromagnetic induction device 81 and the second electromagnetic induction device 82 are disposed in the main body 10 and the sucking unit 20 separately. The first electromagnetic induction device 81 is electrically coupled with the power supply unit 30. When the power supply unit 30 provides power to drive the first electromagnetic induction device 81, the second electromagnetic induction device 82 is also triggered at the same time to enable the lighting unit 60 to emit light. The first electromagnetic induction device 81 and the second electromagnetic induction device 82 are not directly electrically connected with each other, and the first electromagnetic induction device 81 delivers power to the second electromagnetic induction device 82 by an electromagnetic induction manner, so that the second electromagnetic induction device 82 can be triggered to enable the lighting unit 60 to emit light. The process of operating the nasal aspirator 2 of the present disclosure will be described in the following.

In order to use the nasal aspirator 2, the user can press the power switch 71, the power switch 71 then directly drives the lighting unit 60 and the air extracting unit 50 (such as the air pump 40 of the air extracting unit 50) at the same time through the control unit 70, so that the lighting unit 60 emits light to facilitate alignment of the suction head 25 with the nasal cavity for sucking snot. Alternatively, by using the switch, the control unit 70 can also control the lighting unit 60 to drive the light-emitting element 61, and after the suction head 25 is aligned with and inserted into the nasal cavity, the air pump 40 is then driven to suck snot. It is appreciated that, upon design demand, the switch can be used to drive the air extracting unit 50 and the lighting unit 60 at the same time or one after another. It is to be noted that the power switch 71 can enable the power supply unit 30 to trigger the first electromagnetic induction device 81 and the second electromagnetic induction device 82 both, thereby driving the control unit 70; or, after the power switch 71 electrically drives the control unit 70, the power switch 71 can enable the first electromagnetic induction device 81 to trigger the second electromagnetic induction device 82 for then driving the lighting unit 60 and the air extracting unit 50.

Figure 7:
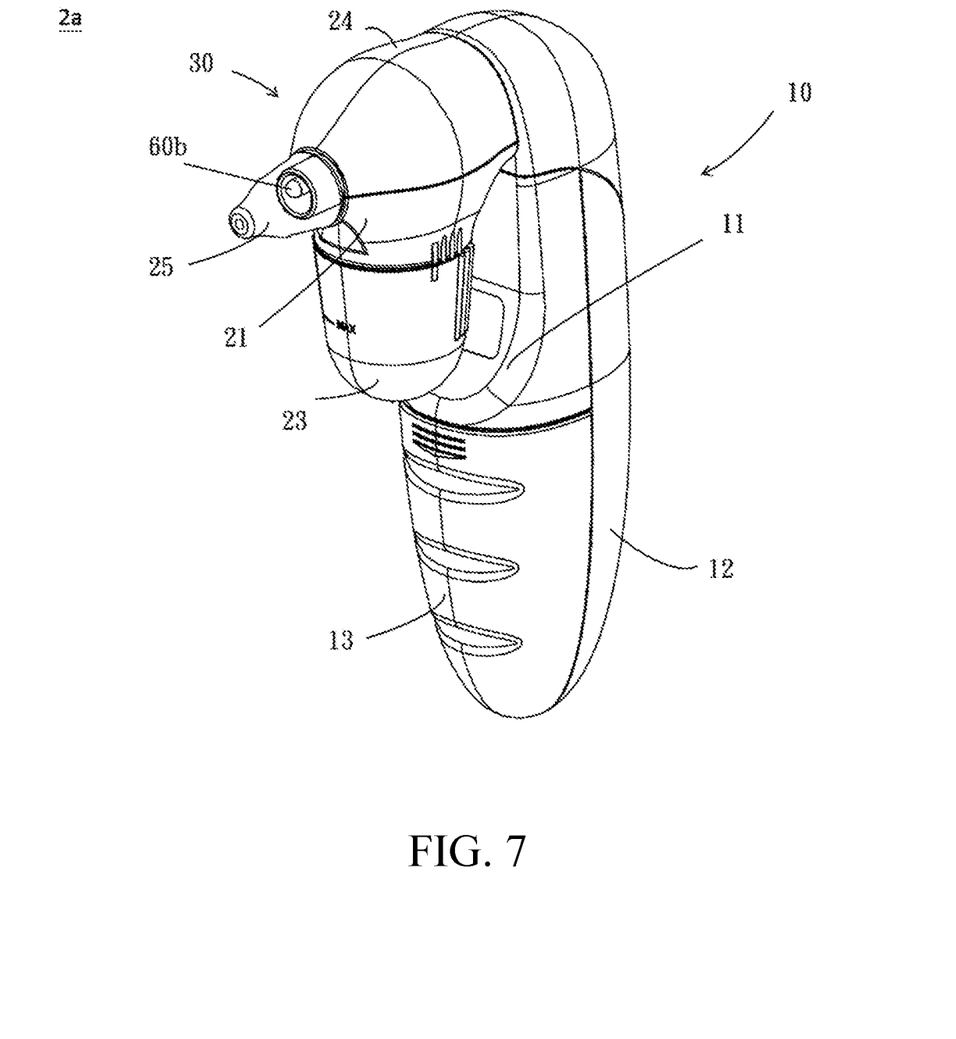
FIG. 7 is a perspective view of modification of the second embodiment of the nasal aspirator of the present disclosure.
Figure 8:
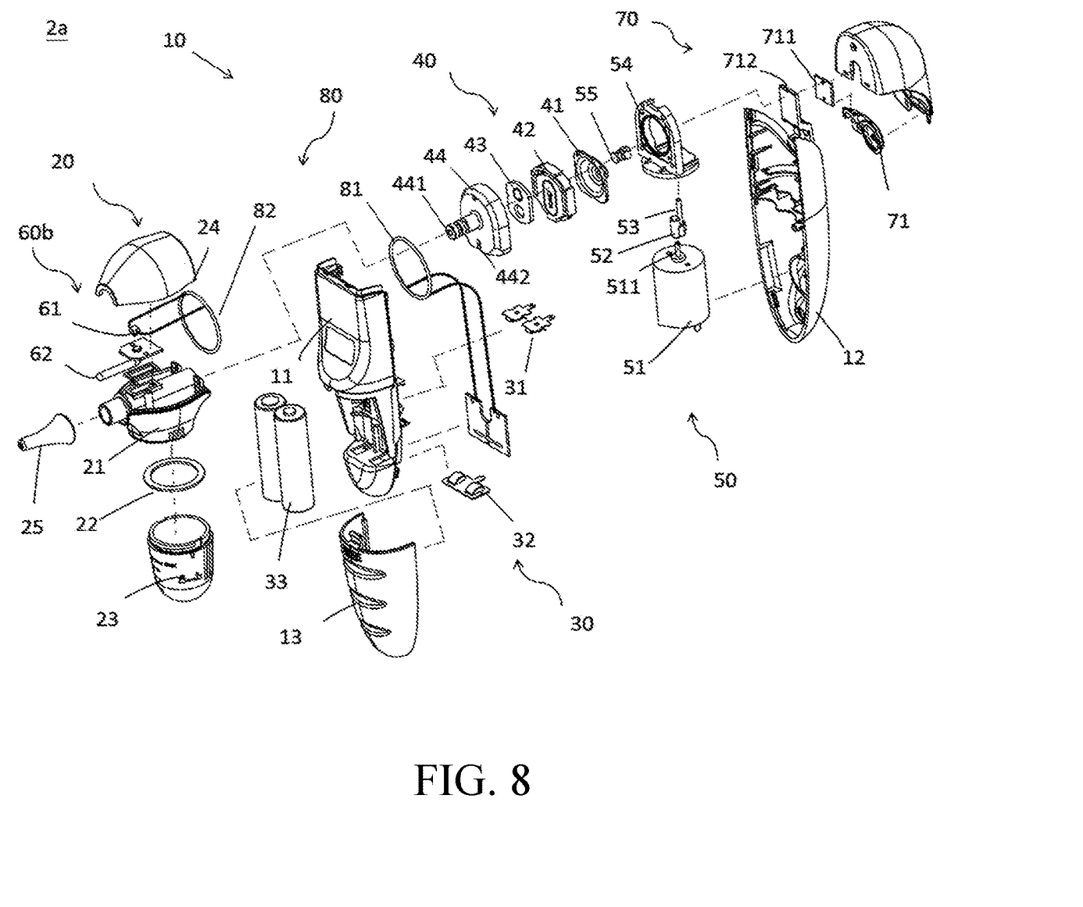
FIG. 8 is an exploded view of modification of the second embodiment of the nasal aspirator of the present disclosure.

Please refer to FIGS. 7 and 8, which show modification of the nasal aspirator 2 of the present disclosure. Major elements of a nasal aspirator 2a are the same as that of the nasal aspirator both, and difference of the nasal aspirator 2a and the nasal aspirator 2 is that the optical conductor 62 of the lighting unit 60b is a light pipe, and the light-emitting element 61 is mounted in the optical conductor 62. By changing configuration of the lighting unit 60b and the sucking unit 20, the lighting unit 60b of the nasal aspirator 2 can be more efficient in light emission.

The present disclosure disclosed herein has been described by means of specific embodiments. However, numerous modifications, variations and enhancements can be made thereto by those skilled in the art without departing from the spirit and scope of the invention set forth in the claims.

What is claimed is:

1. A nasal aspirator with a lighting function, comprising:
a main body;
a power supply unit, disposed in the main body and configured to provide a direct current, including a battery set;
a sucking unit, which is coupled with and extended out of the main body and configured to insert into a nasal cavity;
an air extracting unit, which is disposed in the main body, electrically coupled with the power supply unit, and configured to enable the sucking unit to generate suction;
a lighting unit, disposed in the sucking unit, wherein the power supply unit is configured to drive the air extracting unit and the lighting unit;
a control unit, electrically coupled with the air extracting unit and the lighting unit, wherein the control unit includes a power switch which is configured to enable the power supply unit to provide a power to the air extracting unit in response to an activation of the power switch;
a first electromagnetic induction device, which is disposed in the main body and electrically coupled with the power supply unit; and
a second electromagnetic induction device, which is disposed in the sucking unit and electrically coupled with the lighting unit, wherein the first electromagnetic induction device and the second electromagnetic induction device are not directly electrically coupled with each other, wherein the second electromagnetic induction device and the lighting unit both are not electrically coupled to the power supply unit,
wherein when the power supply unit provides the power to drive the air extracting unit and the first electromagnetic induction device in response to the activation of the power switch, the first electromagnetic induction device delivers a further power to the second electromagnetic induction device in an electromagnetic induction manner by the power provided, wherein the second electromagnetic induction device enables the lighting unit to emit light by the further power delivered, such that the air extracting unit and the lighting unit are driven by the power supply unit at the same time in response to the activation of the power switch.

2. The nasal aspirator according to claim 1, wherein the power supply unit is in contact with the air extracting unit through electrodes to provide the power.

3. The nasal aspirator according to claim 1, wherein the air extracting unit comprises an air pump configured to enable the sucking unit to have a negative pressure function.

4. The nasal aspirator according to claim 1, wherein the sucking unit comprises an optical conductor for conducting light generated from the lighting unit.

5. The nasal aspirator according to claim 4, wherein the optical conductor has a shape selected from the group consisting of an annular shape, a pillar shape, and a tapered shape.

6. The nasal aspirator according to claim 1, wherein the lighting unit comprises a light-emitting element which is a light source selected from the group consisting of a solid state light source and a gaseous light source.

7. The nasal aspirator according to claim 6, wherein the light-emitting element is selected from the group consisting of a light-emitting diode and a bulb.

8. The nasal aspirator according to claim 1, wherein the sucking unit is an optical conductor for conducting light generated from the lighting unit.

9. The nasal aspirator according to claim 1, wherein the sucking unit comprises a light guide material for conducting light generated from the lighting unit.

* * * * *